United States Patent [19]

Benner et al.

[11] Patent Number: 4,648,714
[45] Date of Patent: Mar. 10, 1987

[54] MOLECULAR GAS ANALYSIS BY RAMAN SCATTERING IN INTRACAVITY LASER CONFIGURATION

[75] Inventors: Robert E. Benner; Joseph D. Andrade; Richard A. Van Wagenen; Dwayne R. Westenskow, all of Salt Lake City, Utah

[73] Assignee: University of Utah, Salt Lake City, Utah

[21] Appl. No.: 774,643

[22] Filed: Sep. 11, 1985

[51] Int. Cl.[4] .............................................. G01J 3/44
[52] U.S. Cl. ..................................... 356/301; 356/418
[58] Field of Search ............... 356/300, 301, 302, 308, 356/318, 418; 350/315

[56] References Cited

U.S. PATENT DOCUMENTS

| | | | |
|---|---|---|---|
| 3,704,951 | 12/1972 | Chupp | 356/301 |
| 3,723,007 | 3/1973 | Leonard | 356/301 |
| 3,807,862 | 4/1974 | Hatzenbuhler | 356/301 |
| 3,877,818 | 4/1975 | Button et al. | 356/416 |
| 4,176,916 | 12/1979 | Carpenter | 356/418 X |
| 4,410,271 | 10/1983 | Mathews | 356/301 |

Primary Examiner—Eugene R. LaRoche
Assistant Examiner—David Mis
Attorney, Agent, or Firm—Thorpe, North & Western

[57] ABSTRACT

The concentration of multiple polyatomic gases are determined almost simultaneously by Raman scattering. The gas sample is placed in a sampling cell located in the resonance cavity of a laser and a polarized laser beam having sufficient intensity to produce detectable signals of Raman scattered light is passed through the cell. The scattered light is captured and redirected by means of a reflection mirror located parallel to the axis of the laser beam adjacent to and outside of the cell. Signals of both inelastic Raman scattered light and elastic laser scattered light are collected by a collection lens means opposite the reflection mirror and outside the gas cell. The collection lens is also parallel to the axis of the laser beam. The collected scattered signals are directed onto a laser line rejection filter where the scattered elastic laser signals are filtered out and the inelastic Raman scattered signals are transmitted to come in contact with a rotating filter wheel containing a series of interference filters with each filter being specific to the transmission of one Raman line. The Raman lines passing through the rotating filters are sensed sequentially by a single detector means and amplified and converted into digital electrical pulses which are processed and converted into visual readouts indicative of the concentration of each of the polyatomic molecules in the gas being determined.

20 Claims, 3 Drawing Figures

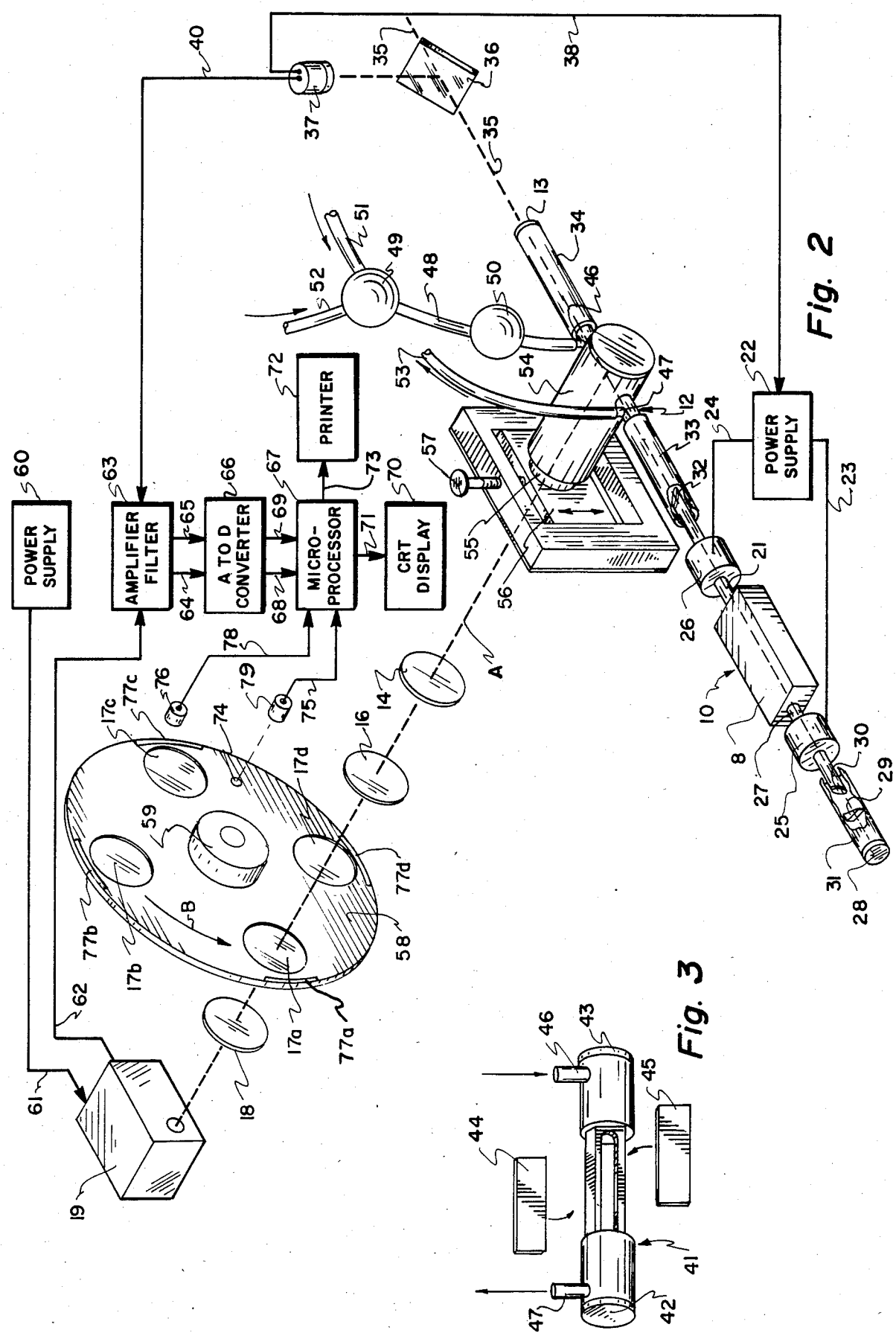

MOLECULAR GAS ANALYSIS BY RAMAN SCATTERING IN INTRACAVITY LASER CONFIGURATION

BACKGROUND OF THE INVENTION

This invention relates to a method and system for the near simultaneous analysis of multiple gases by means of Raman scattering wherein the Raman scattering sample is placed within the laser resonator and a single detector is utilized for quantitating the Raman signals of each gas being analyzed. The invention also relates to a system which does not utilize a spectrometer or spectrograph but rather employs a series of filters which reject the elastically scattered laser line while passing the particular Raman lines of interest. More specifically, this invention relates to a method and system for the detection of multiple respiratory and anesthesia gases by Raman scattering wherein the incident laser beam passes through the gas sample placed in the intracavity of a laser and a rotating filter wheel, containing filters specific for each Raman scatter line of interest, is used to transmit light onto a single appropriate detector for quantitating each specific Raman signal, and thus each gas.

The monitoring of respiratory and anesthetic gases as well as specific cardiac and pulmonary functions which in turn are based upon the uptake and production of specific gases has reached a high standard of technological advancement with the development of sophisticated sensors, transducers, and computers. These monitoring techniques enable quick diagnosis and treatment of unfavorable trends in the condition of a patient and lead to an improved survival rate, early extubation following surgery and a shorter time in the intensive care unit. Applications of respiratory and anesthesia gas monitoring include the measurement of anesthetic uptake, oxygen consumption, and carbon dioxide production These measurements lead to a more scientific basis for the administration of anesthesia. A breath-by-breath analysis of multiple respiratory and anesthesia gases of patients in the operating room, and of respiratory gases in intensive care and other critical situations can often facilitate diagnosis and treatment, anticipate and prevent the development of oncoming problems and otherwise provide instant data for physicians and other health care personnel to use in therapeutic situations. The same may be said of the breath-by-breath analysis of gas mixtures used for noninvasive determination of cardiac output and lung function.

Respiration monitoring of the critically ill patient is now available in intensive care units. Multiple bed sampling techniques make feasible the use of an expensive, multiplexed mass spectrometer because it can be shared among a number of patients. Since the unit is large and not easily moved from room to room, it is generally placed in a remote location and lengthy capillary tubes are used to connect the patients. This tube transport system increases the possibility of gas sample mixing, time delay, and disconnections and poses inherent limitations for use in anesthesia, critical care and medical research Mass spectrometry also has only limited flexibility in the study of gas mixtures. Alternatively, there are a variety of gas detectors based upon several different physical principles which, taken together, can measure anesthesia and respiratory gases. Their problems are: high aggregate cost, bulkiness and poor data integration into one comprehensive display of patient parameters.

An alternative proposed for use in monitoring several gases in critical care situations is based on Raman light scattering. The Raman light scattering effect relies on the interaction of monochromatic light with the vibrational/rotational modes of molecules to produce scattered light which is frequency shifted from that of the incident radiation by an amount corresponding to the vibrational/rotational energies of the scattering molecules. Since these energies are species-specific, an analysis of the various frequency components present in the Raman scattering spectrum provides chemical identification of the gases present in the scattering volume. The intensity of the various frequency components or Raman lines provides quantitation of the gases present providing suitable calibrations have been made. The relative sensitivity to the different gases remains absolutely fixed, eliminating frequent calibration requirements.

Raman techniques have been widely used for atmospheric monitoring and for combustion applications. Sensitivities better than 1 ppm have been demonstrated. Typical application of Raman scattering analysis coupled with computer assisted signal processing techniques is reported in Lapp et al., "Laser Raman Gas Diagnostics", Plenum Press, New York/London, 1974.

Raman scattering analytical techniques are also described in the patent literature. Chupp, U.S. Pat. No. 3,704,951 teaches laser Raman spectroscopy utilizing a sampling cell with a multi-pass configuration. A laser beam enters into the cell configuration of concave mirrors facing each other such that there is a multiple reflection of the laser beam between the mirrors to accomplish the required optical power density enhancement in the sampling area and subsequent signal enhancement. This device and accompanying technique is limited in that it provides for analysis through only a single detector. Hence, simultaneous monitoring of multiple gases is not possible. Moreover, this device is intended for use primarily with liquids and has only limited application for gases. Also, the alignment of the mirrors for optimal signal is exceeding delicate. Finally, the beam size in the sampling region must be quite small to maintain low sample volume and subsequently high signal response time. A multimirror approach makes this difficult, if not impossible, given the optics of such a system.

Hatzenbuhler, U.S. Pat. No. 3,807,862 also teaches a specific application of Raman spectroscopy in which a fluid sample is subjected to a laser beam and only a single Raman line is evaluated. In other words, there is no teaching of a technique for the determination of multiple gases.

Leonard, U.S Pat. No. 3,723,007 is drawn to a method for the remote sensing of gas concentrations through use of a high-energy pulsed laser and a mirror telescope, using a grid polychromator. This system requires a laser output in the 10 kW range and is unsuitable for general application. Moreover, the use of an expensive spectrometer presents an obstacle in the way of cost-beneficial production of the device.

A more recent and effective system for the simultaneous detection of multiple gases is taught in Albrecht, et al., German Pat. No. DE 27 23 939 C2. This patent also utilizes a multi-pass cell to constrain the laser radiation in a region between two concave mirrors for signal enhancement but utilizes an unpolarized laser beam to provide a 360° monitoring geometry for the Raman scattered light. A series of six detectors, each accompanied by an interference filter comprised of one broadband and one gas-specific filter, are provided to collect six separate Raman lines for the simultaneous monitoring of six different gas components. This method, while monitoring multiple gases simultaneously, requires six separate detectors including separate photomultiplier tubes and recording instruments. Such a complex system is bulky and expensive. Moreover, since the orientation of the six detectors described in the German patent could not be expected to exactly image in the same area, the acquisition of all gas concentrations could not be from exactly the same point in the gas flow stream.

OBJECTS AND SUMMARY OF THE INVENTION

It is an object of the present invention to provide a system and method for the near simultaneous monitoring of multiple gases by means of Raman scattering through the use of an intracavity sampling cell and a single detector receiving Raman line spectra from a rotating filter wheel containing multiple filters through which Raman scattered light passes wherein each filter is specific to the gas species being detected.

It is also an object of this invention to utilize a gas sampling cell located within the resonance cavity of the laser to enhance the laser power wherein the sampling volume is small and continuous.

Another object of the present invention is to provide a system for continuous analysis and quantitation of multiple gases through Raman scattering by means of a combination of an intracavity gas sampling cell and a spherical reflector to enhance laser power and a rotating filter wheel located to receive and serially pass species specific Raman line signals to a single detector which serially quantitates each gas to be detected.

These and other objects are made possible by means of a Raman scattering system and method of utilizing that system. The system comprises a laser source containing a gas sampling cell located within the resonance cavity of the laser for enhancing the Raman scattering signal. A reflection mirror is located adjacent to the cell and normal to the laser beam to capture some proportion of the Raman scattered light solid angle and direct it towards the collection and detection portions of the system. The collected Raman scattered light is directed successively onto and through a collection lens, or a series of antireflection coated collection lenses, and a laser line rejection filter to attenuate the elastically scattered laser line and transmit the inelastically scattered Raman lines arising from the gas molecules being sampled. The Raman lines are then serially detected by means of a rotating filter wheel containing a series of narrow band interference filters. Each filter is chosen to pass along one Raman scatter line corresponding to a discrete molecular species.

A lens, or a series of antireflection coated lenses, behind the filter wheel is used to focus the transmitted light onto a detector which both converts the light to an electronic signal and amplifies it by a factor of $10^5$–$10^6$. Typical of amplification and detection means is a photomultiplier tube (PMT) used in conjunction with photon counting or photocurrent electronics, or a variety of solid state photodetectors such as but not limited to avalanche photodiodes. Thus, as the filter wheel rotates from filter to filter, various gases are sensed and their corresponding concentrations determined after suitable calibrations have been made. With each rotation of the wheel a value for each gas can be visually displayed or printed out. Hence, the determination of each gas, while serial, is substantially simultaneous and instantaneous because the wheel is rapidly rotating, i.e. several hundred revolutions per minute (rpm).

DESCRIPTION OF THE DRAWINGS

FIG. 2 is a schematic diagram showing one complete embodiment of a laser Raman scattering sampling and detection system.

FIG. 3 is a perspective view of an intracavity gas sampling cell as utilized in the system shown in FIG. 2 with side windows removed.

DETAILED DESCRIPTION OF THE INVENTION

Figure 1:
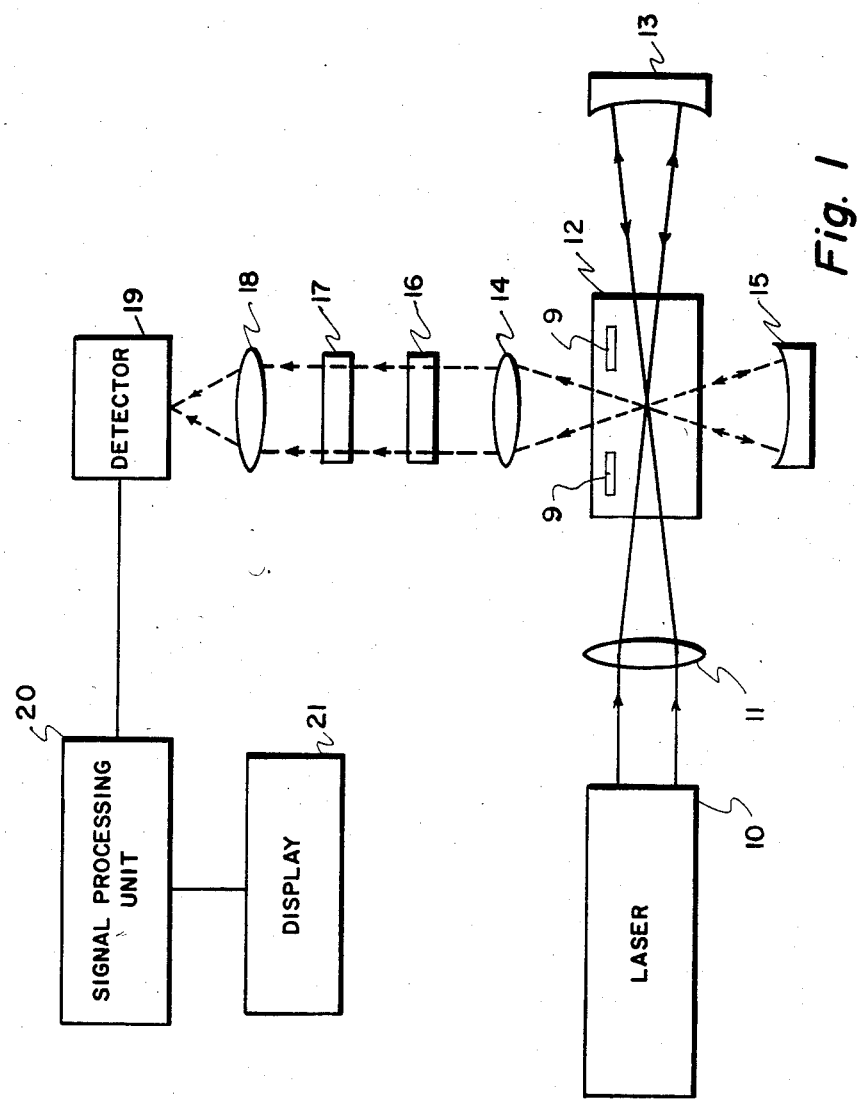
FIG. 1 is a schematic representation of one embodiment of the invention showing an intracavity gas sampling cell, Raman light collection and filtering means and a detection system.

There is shown in FIGS. 1–3 a complete and preferred embodiment of the invention.

The systems broadly consists of a laser 10, to be described in detail in FIG. 2, which directs a polarized laser beam, such as a cw Ar+ laser (tens of milliwatts extracavity power at 488 nm) through a focusing lens 11 into a sampling gas cell 12 containing the gases to be analyzed all located within the resonating cavity of the laser. Alternatively, focusing lens 11 is not necessarily required should the diameter of the laser beam be sufficiently small to traverse the gas cell and the small size of a focused beam not need to be imaged onto the entrance slit of a monochromator.

There are at least two advantages to be gained by placing the sample within the laser resonator. The intracavity laser power is immediately higher than the extracavity laser power by a factor of $[1+R]/T$, where R and T are the reflectivity and transmission of the laser output mirror 13. The other advantage is obtained by increasing the reflectivity of the output mirror 13 to further enhance the intracavity power. An intracavity laser Raman spectrometer, somewhat different from that disclosed in this specification, is described by Hercher, et al., "Applied Spectroscopy", Vol. 32, No. 3, (1978) pp. 298–301.

The power of the intracavity laser beam interacting with the gas molecules can thus be enhanced by a factor up to about 100 within the intracavity gas cell to provide the necessary high excitation intensity within the scattering volume at the center of the cell 12. The Raman scattered light, which is emitted nonisotropically in all directions, is then collected over as large a solid angle as possible by collection lens 14 located perpendicular to the axis of the cylinder formed by the incident laser light. Collection lens 14 may actually consist of a series of optimally configured lens elements all antireflection coated. One example would be a fast (f/1.2) camera lens. A reflection mirror 15 captures and redirects a proportion of the Raman scattered light back into the collections lens 14 and serves to increase the collection of Raman scattered light by a factor of about 2. The reflection mirror is oriented perpendicularly to the axis of the laser beam and at a distance from it equal to its radius of curvature. Such a mirror may be either spherical or cylindrical in shape.

A particular advantage of a preferred embodiment of this invention is that it is not absolutely necessary to focus the laser beam to a narrow waist inside the gas cell as in prior art applications. The reason for this is that a grating spectrometer having a narrow entrance slit is not utilized. Thus, the optical system need not image a small beam waist upon a narrow entrance slit. Therefore, focusing lens 11 as found in FIG. 1 is not necessary in this embodiment. Lens 14 and reflection mirror 15 function optimally to collect light from a point in the laser beam assuming lens 14 is a spherical lens. Light collection from a specified point with good stray light rejection, if desired, may be facilitated by use of iris diaphram 9 optimally placed in the gas cell 12 to reject light from all other areas of the laser beam.

The collection lens must be properly aligned with respect to the laser beam as will be better described in conjunction with FIG. 2. Elastically and inelastically scattered light collected by lens 14 is directed to one or more serially oriented high rejection laser line filter(s) 16. Filter(s) 16 greatly attenuates the elastically scattered laser line to minimize interference in the Raman or inelastically scattered light and transmits the inelastically scattered Raman lines arising from the incident laser beam interacting with the sample gas and corresponding to the vibrational/rotional energies of the scattering molecules.

When focusing lens 11 is eliminated and iris diaphram 9 is used to facilitate light collection from a point in the beam all light rays exiting collection lens 14 travel parallel to each other and intercept line rejection filter(s) 16 and interference filter 17 perpendicularly. The result of this configuration is excellent rejection of the elastically scattered laser light and good transmission of the Raman signal with a subsequently good signal to stray light ratio, but with relatively low signal.

A particularly preferred approach is to eliminate both focusing lens 11 and iris diaphram 9 of FIG. 1. In this mode spherical collection lens 14 serves to collect signal from the entire laser beam in gas cell 12. In practical application collection is from a beam about 1 mm. in diameter and 15 mm. in length. The result is that the spherical collection lens 14 and reflection mirror 15, if spherical, collect much more light (both elastic and inelastic) so the signal is much higher. However, they do not function optimally in this mode because some of the collected light hits filters 16 and 17 nonnormally resulting in high stray light signal transmitted to the detector system so that the signal to stray light ratio is relatively high. One possible alternative to use of a spherical collection lens 14 would be a clyindrical collection lens in the same position having an identical focal length and "f" number. Such a lens would more efficiently collect the laser line and produce a collimated output for the line rejection filter(s) 16. The same may be said for an alternative to a spherical mirror 15. That is, it may be a cylindrical mirror which would more efficiently redirect a solid angle of the complete length of the laser beam sampled rather than a point.

Since each polyatomic gaseous molecule causes a frequency shift from that of the incident radiation by an amount corresponding to the vibrational/rotational energies of that molecule and is species specific, an analysis of the frequency components present in the Raman scattered light provides identification and quantification of the gases present in the scattering volume. Quantification is determined from measured Raman signal intensities using calibration reference gases and known Raman scattering cross sections.

The expected Raman signal intensity, I, in photoelectron pulses/second is given by Equation 1 as follows:

$$I = 2P/\epsilon \rho \sigma Q X S_o T_o T_f T_L T_{IF}$$

where p = is the power in the analysis region(assume 2 watts)

$\epsilon$ = excitation photon energy (@488nm, $\epsilon = 4.1 \times 10^{-19}$ J)

$\rho$ = molecular concentration($= 2.49 \times 10^{19}$ molecules $N_2/cm^2$ at STP)

$\Sigma$ = Raman scattering cross section for $N_2$ ($5.4 \times 10^{-31}$ cm/sr)

Q = PTM quantum efficiency (4%)

X = gas scattering cross section relative to $N_2$ (1)

$S_o$ = collection optics solid angle (0.27 sr)

$T_o$ = collection optics transmission (0.9)

$T_c$ = focusing optics transmission (0.9)

$T_l$ = laser line filter transmission (0.7)

$T_n$ = interference filter transmission (0.7)

Substituting these values in Equation 1 yields 562,300 photoelectron pulses/second or counts/second. Assuming the PMT photocathode is 4% efficient in converting photons to photoelectrons and that the overall tube gain is $3.8 \times 10^6$ then each photon induced PMT photoelectron pulse carries 152,000 electrons which flow as a photocurrent. In the above example of pure $N_2$ gas at STP conditions there is a current of $8.547 \times 10^{10}$ electrons/second. Given values of 96,500 coulombs/second for the Faraday constant and $6 \times 10^{23}$ electrons/mole for Avogadros Number there is obtained a value of $14 \times 10^{-9}$ coulombs/second or 14 nanoamps of photocurrent.

In order to quantify each gas species, a filter wheel (described in detail in conjunction with FIG. 2) containing a series of narrow band interference filters, is located just behind filter(s) 16. As shown in FIG. 1 this is represented by a specific interference filter 17 which is chosen to pass alone one Raman scatter line corresponding to a discrete molecular species.

Since primary interest on this invention is focused on respiratory and anesthesia gases the following table illustrates the Raman Stokes frequency shifts and relative scattering cross sections for those gases of interest.

TABLE I

| Gas Species | Frequency Shift ($CM^{-1}$) | Relative Scattering Cross-Section |
|---|---|---|
| $N_2$ | 2331 | 1.0 |
| $O_2$ | 1555 | 1.0 |
| CO | 2143 | 0.9 |
| $CO_2$ | 1285 | 0.8 |
|  | 1388 | 1.2 |
| $N_2O$ | 1285 | 1.8 |
|  | 2224 | 0.5 |
| $H_2O$ | 3652 | 2.8 |
| Isoforane | 772–904 (triplet) | 1.8 |
| Enflurane | 817 | 0.5 |
| Halothane | 717 | 1.4 |

The Raman scatter light having the selected frequency passes through intereference filter 17 and is imaged onto a detector by means of a focusing lens 18. The detector can be any device capable of receiving the signal and amplifying and processing it into useful data. Represented in FIG. 1 is a photomultiplier tube (PMT) 19 which is connected to a signal processing unit 20 which may be a photon counter, a photocurrent amplifier or other device including a central processing unit or microprocessor which can further amplify, process and quantitate the Raman signal into useful analog or digital data which is then displayed on display device 21, e.g., a CRT screen and/or printer. Table I shows that those gases of interest generally have scattering cross sections >1, that water vapor does not interfere with the signals and that there is rarely any spectral overlap between the Raman spectra provided that narrow (1 nm full width half maximum) band pass interference filters with high (>1,000) out of band rejection are used.

A preferred embodiment of the invention is illustrated in FIGS. 2 and 3. The components schematically illustrated in FIG. 1 will be identified by the same numerals in these figures.

The laser source 10 comprises a power supply 22 connected by lines 23 and 24 to a cathode 25 and anode 26 which surround the ends of and activate a plasma tube 27 containing argon gas. A radiator 8 and fan system (not shown)thermally connects and surrounds the plasma tube for cooling purposes. One end of the laser's resonant cavity, adjacent to the plasma tube 27, is defined by a high relefectivity mirror 28 and a prism 29 for wavelength selection. At the end of plasma tube 27 is a Brewster window 30. A dust tight sleeve 31 surrounds the mirror, prism, Brewster window and end of the plasma tube to protect these components from particulate and molecular contamination. At the opposite end of the plasma tube is another Brewster window 32. Brewster windows 30 and 32 cooperate to transmit the prism selected polarized wavelength of the laser beam being pumped through the resonating cavity of the laser without substantial loss.

The remainder of the laser cavity is defined by the gas cell 12 and output coupler mirror 13. A sleeve 33 connects the plasma tube 27 and Brewster window 32 with one end of gas cell 12 and another sleeve 34 connects the output coupler mirror 13 and the other end of the gas cell to prevent dust or other contamination from entering into the resonance chamber and subsequently fouling mirrors and windows causing a subsequent attenuation of intracavity resonance and power.

Mirror 28 is highly reflective. Output coupler mirror 13 also has high reflectivity for the laser line of interest. Typically it will be about 99% reflective. The extra cavity beam 35 leaving mirror 13 is intercepted by a beam splitter 36 which directs a small portion of the beam to a photodiode 37 which is serially connected to laser power supply 22 by signal line 38 and to one channel of a 2 channel electronic amplifier-filter combination 63 by signal line 40. The remaining portion of the beam 35 enters an optical extinguisher (not shown). Via diode 37, optical feedback to the power supply 22 provides correction for long term (typically seconds or greater) fluctuations in laser power. Photo diode 37 feedback to the two channel amplifier-filter 63 provides correction for high frequency fluctuations in the optical output power of the laser ( typically 1 millisecond to 1 second variations).

Since the resonance cavity of the laser is located between mirrors 28 and 13 the placement of gas cell 12 between the end of plasma tube 27 and mirror 13 is termed "intracavity".

One embodiment of a gas sampling cell 12 is shown in detail in FIG. 3 and consists of a framework having a hollow interior, means for bringing a gas sample into and out of the interior and windows through which both the incident laser beam and the scattered Raman light may pass. The shape, i.e. cylindrical, rectangular, etc., is not important as long as the functional criteria are met. The cell shown consists of a hollow housing 41 generally cylindrical in shape having its axis oriented to accomodate the passage of the laser beam through the axial center. At either end of the housing are optical windows 42 and 43. Windows 42 and 43 are coated with a highly efficient narrow band antireflection coating, i.e. a "V"-coating, for the particular wavelength of the laser. "V"-coatings are multilayer antireflection coatings which reduce the reflectance of an optical component to near-zero for one very specific wavelength and are generally intended for use at normal or near normal incidence. Hence, windows 42 and 43 are parallel to each other and substantially normal to the axis of the housing and the laser beam. Maximun intracavity power power is achieved if windows 42 and 43 are slightly tilted to be non-normal to the laser. By slightly tilted is meant that the windows do not vary more than about 10° in either direction from a position perpendicular to the laser beam. Hence the term "substantially normal" is used. The windows, if tilted, will always be tilted in the same direction so as to remain parallel to each other. Such coatings will acheive maximum reflectances of not more than about 0.25% and are generally effective to allow only about 0.1% reflectance at the specified wavelength. Thus, they do not appreciably interfere with the transmittances of the laser beam through the resonating cavity of the laser. The purpose of windows 42 and 43 is two-fold; first, they constrain the sample gas within cell 12 and thus minimize sample volume and maximize response time, and, second, they serve to isolate the Brewster window 32 and the output mirror 13 from possible contamination arising from the gas sample. The hollow housing 41 at the central portion of the cell also contains optical windows 44 and 45. The alignment of these windows is not as critical as the end optical windows 42 and 43. However, they are preferably parallel to each other. These optical side windows are also preferably coated with a broad band antireflection coating. Since these windows must transmit the Raman scattered light to a detector they must pass the desired wavelengths. Hence, a high efficiency broad band antireflection coating such as HEB-BAR(tm) is appropriate. V Band and broad band coatings are multilayer dielectric films, comprising alternate layers of various refractive index transparent materials, combined in such a way to reduce the overall reflectance to an extremely low level for the spectral range covered. Over the broad band range the reflectance will not generally exceed 1.0% and will generally be below 0.6%. The cell contains an inlet 46 and an outlet 47 for passing the sample gas through the cell. The cell design is very important in that it allows for a very small volume of gas, typically between about 0.1 and 1.0 cubic centimeters, to constantly be passed through the laser beam. On the other hand, it is well adapted for use in a batch type operation in that only a small sample is required of any given gas to be analyzed. The inlet 46 is connected via supply line 48 to a solenoid valve 49 and sample gas is drawn into the cell interior by means of an air pump 50. Depending upon the position of the solenoid, room air may be drawn via line 51 into the cell for system calibration against nitrogen gas. Alternatively, a respiratory gas, or other sample gas, may be drawn via line 52 from the airway of a patient or other sample source by air pump 50. Tubing 53 connected to cell outlet 47 conveys sampled gas out of the cell for disposal or reintroduction into a patient's airway or for collection and storage.

The gas cell 12 also becomes part of the Raman scattered light collection system and is located within collection housing 54 as shown in FIG. 2. The interior of collection housing 54 comprises gas cell 12 oriented with its axis parallel and coincidental with the intracavity laser beam, a spherical collection mirror 15, and, if used, an iris diaphram 9. Housing 54 is tubular and is oriented with its axis perpendicular to the laser beam. Housing 54 telescopes over interface tube 55 via a close frictional fit. Interface tube 55 is rigidly affixed to vertical translation stage 56. Collection housing 54, interface tube 55 and translation stage 56 function together to provide necessary alignment of gas cell 12 to both the intracavity laser beam and the collection lens 14 for optimal signal.

It is important that the gas cell be properly aligned and fixed in position to attain the optimal signal. Therefore, some adjustments are made and components fixed securely in place at the time of installation of the cell. When placing the gas cell in housing 54 it may be rotated about an axis parallel and coincident to the laser beam until the maximum optical signal is obtained. Gas cell 12 is then fixedly secured into housing 54 by any suitable mechanical or chemical means such as set screws or adhesives. A horizontal adjustment in a plane perpendicular to the laser beam may be made to orient collection housing 54 and gas cell 12 with respect to the collection lens 14 by sliding the housing 54 in or out of the interface tube 55. At the same time the gas cell may be oriented with respect to the laser beam by axially rotating the collection housing 54 about the interface tube 55. The collection housing 54 can then be fixedly secured to the interface tube by suitable mechanical or chemical means such as set screws or adhesives. It may be advantageous to utilize set screws or other mechanical means which will allow variable adjustment of the collection housing and gas cell as needed to attain the maximum optical signal. Finally, translation stage 56, to which interface tube 55 is secured, functions to position the collection housing 54 and its associated attached elements with respect to both the laser beam and the collection lens 14 by vertical translation effected by turning a screw 57 which works against a spring (not shown) located below the movable element of the translation stage. Following the obtaining of the maximum signal the movable element of the translation stage containing the interface tube 55 is also secured in position by suitable mechanical means or by adhesives.

Serially located along the light collection path indicated by broken line A in FIG. 2 after the collection housing is collection lens 14, laser line rejection filter(s) 16 and interference filter(s) 17a, 17b, 17c and 17d. Interference filters are mounted in a filter wheel 58 having a drive motor 59 associated therewith. Filter wheel 58 rotates about an axis parallel to the collection path represented by line A in a direction indicated by the directional arrow B and sequentially brings filters 17a–d into the collection pathway. The drive motor is selected to drive the filter wheel at the desired rpm. Focusing lens 18 is located behind filter wheel 58 to image the Raman line exiting a filter 17 into a detector 19.

The number of filter(s) 17 in filter wheel 58 may vary according to the number of molecular species to be analyzed. The only limit on the number of filters is the capability of the data processing system. Obviously, the greater the number of filters, the greater will be the diameter of the filter wheel. The diameter of each filter in the wheel must be sufficient to allow sufficient Raman line input into the detection system as will be subsequently discussed.

Detector 19 may be any suitable state of the art detector such as a photo diode, intensified diode array or photomultiplier tube powered by an appropriate power supply 60 via line 61.

The photons received by detector 19 are converted to electric current or voltage and amplified and sent by line 62 as photocurrent or photo voltage to a 2 channel amplifier-filter 63 where the signal is further amplified and the noise is appreciably filtered out to insure good signal fidelity. The signals are then sent by lines 64 and 65 to an A/D converter 66 where the analog signals are converted into standard digital pulses and relayed to microporcessor 67 via lines 68 and 69. The processing of the specific Raman lines entering detector 19 into useful data is accomplished by known means and the signals entering micropressor 67 may be processed by software to provide the desired data which are then sent to a digital or analog CRT display 70 via line 71 or to a printer 72 through line 73.

While state of the art techniques are used to process the data, the manner in which the data are collected, processed and displayed may be varied to provide the needs of the end user.

Filter wheel 58 will be set to operate at a specific rpm consistent with the needs of the detection system. With current technology the sampling time required of any given Raman line passing through filters 17 into detector 19 to provide useful data of gas concentration need be measured in terms of milliseconds.

FIG. 2 is illustrative of two separate Raman line sampling and processing techniques.

In one technique, photodiode 79 located in filter wheel housing (not shown) is situated to sense reference dot 74 on filter wheel 58 during each rotation thereof to signal to microprocessor 67 via line 75 the start of a new sampling cycle. For purposes of illustration it will be arbitrarily assumed that the filter wheel is operating at 360 rpm. There would then be six sample cycles each second or one cycle every 166.667 milliseconds. Also assuming that the filter wheel is divided into sixteen sample areas consisting of alternating filters and blanks, the wheel would contain eight interference filters and eight blanks. For reference purposes (dark reference signal for PMT) one filter will be black leaving seven sample interference filters to detect seven distinct Raman lines. Now, assume the microprocessor is programmed to process data in 256 increments per revolution of the filter wheel, there would be an increment processed every 0.65 milliseconds and 16 increments per interference filter. At such high speed the data processed is substantailly instantaneous and continuous. The data can be reported to the microprocessor 67 in discrete time increments (650 microseconds), or time averaged by a suitable electronic filter circuit (i.e. 16×0.65 microseconds=10.4 milliseconds) or stored and averaged over a designated number of filter wheel revolutions (e.g. each 6 revolutions=one second) or over each breath cycle.

A second technique for data processing involves the use of a photodiode 76 located in the wheel housing (not shown) which signals a reference line 77a, 77b, 77c or 77d located on the filter wheel the arc length of which is coincident with the passage of a Raman line through an interference filter 17a, 17b, 17c and 17d, respectively. A signal passing to microprocessor 67 via line 78 from photodiode 76 would tell the microprocessor when to start and stop collecting data for a given interference filter. That data would then be averaged, filtered and digitally reported as a single number. Again, assume the filter wheel is divided into sixteen portions containing 8 filters and 8 blanks and that one filter is black to indicate a reference position. Seven gas samples would be processed with each revolution of the filter wheel.

From the above it is obvious that different numbers of interference filters could be utilized and that the detection, amplification, signal transfer and processing times and capabilities of the detection system could be selected to meet the required data output.

From the above description it is obvious that the present invention presents many advantages over the prior art. Unlike German Pat. No. DE 27 23 939 C2 the filter wheel approach provides much higher signal intensity and only one detector. Moreover, the present invention provides for use of a single reflection or collection mirror and collection lens to collect Raman scatter of all gas concentrations from the same point in a gas flow stream. The six collection lenses and detectors of the German patent are reduced to a single collection lens, one reflection or collection mirror and one detector. In addition, an expensive multi-pass cell outside the laser cavity which requires high tolerance mirrors has been replaced with an intracavity cell requiring two parallel windows with a V-band antireflection coating.

It should also be stressed that the present invention is also removed from the teaching of the German patent in that the German patent makes use of an unpolarized laser beam whereas the present invention requires a polarized intracavity laser beam. Optimal collection of the maximum Raman signal is accomplished by orienting the collection lens and reflection (i.e. collection) mirror axes normal to the polarization of the beam's electric field vector.

The system and process described herein was developed primarily for monitoring respiratory and anesthesia gases. However, it may also be useful for monitoring blood and tissue gases (in conjunction with a suitable sampling catheter), gases used for lung function and cardiac output determinations, hazardous gases in the work place, for detecting leaks in chemical process plants, for monitoring levels of suspected chemical and environmental pollutants and in other applications where polyatomic gaseous molecules are to be detected and measured.

In tests made the detected signal levels for the diatomic molecules, N2, O2, CO2, and CO are approximately 500,000 counts/second (14 nanoamps) for pure gases using point source collection via an iris diaphragm and about 5,000,000 cps (140 nanoamps) for collection from the entire laser beam in the gas cell.

While the above presents several working embodiments of the invention there are others which will be obvious to those skilled in the art. The invention is not to be limited to the embodiments specifically described but is to be interpreted only in conjunction with the scope of the appended claims and their functional equivalents.

I claim:

1. A system for the near simultaneous analysis and quantitation of selected multiple polyatomic gases in a gas sample by Raman light scattering comprising in combination;

(a) laser means capable of producing a polarized laser beam of a selected wavelength containing a laser cavity said laser cavity containing a plasma tube and wherein one end of said laser cavity contains a high reflectivity output coupler mirror;

(b) a gas sampling cell located within said laser cavity between said plasma tube and said output coupler mirror, said cell having opposing parallel end windows interconnected by a continuous sidewall, said end windows and sidewall defining a longitudinal gas chamber oriented such that, when said laser beam is activated, the laser beam is coincident with and traverses the axis of said longitudinal gas chamber, said end windows being positioned to be substantially normal to the axis of the longitudinal gas cell chamber, said cell also having opposing, aligned side windows in said sidewall parallel to and on either side of the axis of said longitudinal gas chamber, said gas cell further containing inlet and outlet means communicating with said chamber to pass a sample gas through said cell;

(c) a reflection mirror positioned adjacent to and outside of said gas cell parallel to and in alignment with said side windows on one side thereof to capture and redirect a proportion of scattered elastic laser light and inelastic Raman light through said side windows, (d) collection lens means positioned parallel to and in alignment with said side windows outside said gas cell and on the side opposite from said reflection mirror to collect elastic laser scattered light and inelastic Raman light passing through said side windows, (e) laser line rejection filter means positioned to receive the scattered light passing through said collection lens means, said filter being selected to reject elastic laser scattered light passing through said collection lens means while allowing the transmission of inelastic Raman scattered light, (f) a rotatable filter wheel containing a series of interference filters wherein each interference filter is selected to transmit only a single Raman spectra line of a predetermined wavelength, said filter wheel being positioned such that, as it rotates, each interference filter will sequentially receive Raman scattered light passing through said laser line rejection filter means;

(g) detection and amplification means for sequentially receiving Raman line signals passing through each of said interference filters and converting said signals to digital electrical pulses;

(h) processing means for intrepreting said digital electrical pulses and converting them to visual readouts indicative of the concentration of each of said selected polyatomic molecular gases in said sample; and (i) power means to operate said laser means, rotating filter wheel, detection and amplification means and processing means.

2. A system according to claim 1 wherein said end windows are coated with an antireflection coating specific to the selected wavelength of the laser beam.

3. A system according to claim 1 wherein said reflection mirror and output coupler mirror are of high reflectivity.

4. A system according to claim 3 wherein said reflection mirror has a radius of curvature and is located relative to the laser beam at a distance from said beam equal to the radius of curvature of said mirror.

5. A system according to claim 4 wherein said reflection mirror is a spherical mirror.

6. A system according to claim 4 wherein said reflection mirror is a cylindrical mirror.

7. A system according to claim 1 wherein said side windows in said gas cell are coated with a broad band antireflection coating adapted to pass desired wavelengths of inelastic Raman scattered light.

8. A system according to claim 1 wherein said filter wheel and processing means are signally connected such that, as single Raman line signals pass through each interference filter, the processing means determines which polyatomic gaseous molecule is being analyzed.

9. A system according to claim 8 wherein said filter wheel contains a series of alternating interference filters and blanks and wherein one of said interference filters is a reference filter.

10. A system according to claim 1 wherein said output coupler mirror allows passage of an extracavity laser beam when said laser beam is activated and wherein means are located to receive said extracavity laser beam signals and convert said signals to current which is directed to one channel of a two channel current amplifier-filter for simultaneous correlation with photocurrent signal in a second channel of said amplifier-filter to correct Raman signal intensity for random fluctuation in laser optical power.

11. A method for the near simultaneous and instantaneous determination of the concentration of multiple polyatomic gas molecules in a gas sample comprising;
   (a) introducing said gas sample into a gas sampling cell located within the resonance cavity of a laser;
   (b) subjecting said gas sample in said laser cavity to a polarized laser beam of selected wavelength and having sufficient intensity to produce detectable signals of inelastic Raman scattered light,
   (c) capturing and redirecting signals of both inelastic Raman scattered light and elastic laser scattered light in a plane normal to the axis of said laser beam by means of a reflection mirror located adjacent to and outside of said gas cell said reflection mirror being parallel to the axis of said laser beam,
   (d) collecting signals of both inelastic Raman scattered light and elastic laser scattered light by collection lens means located opposite said reflection mirror said collection lens means also being parallel to the axis of said laser beam and in alignment with said reflection mirror,
   (e) directing said signals of both inelastic Raman scattered light and elastic laser scattered light onto a laser line rejection filter wherein scattered elastic laser light signals are rejected and signals of inelastic Raman scattered light are transmitted;
   (f) subjecting said signals of Raman scattered light to a rotating filter wheel containing a series of interference filters wherein each interference filter is specific for the transmission of a single Raman line,
   (g) sequentially sensing single Raman line signals passing through the interference filters of said filter wheel by detection and amplification means and converting said signals into digital electrical pulses
   (h) sequentially processing said digital electrical pulses in processing means and converting them to visual readouts indicative of the concentration of each of said polyatomic molecules in said gas sample being determined.

12. A method according to claim 11 wherein said polyatomic gases are members selected from the group consisting of respiratory and anesthetic gases.

13. A method according to claim 12 wherein said polyatomic gases are members selected from the group consisting of nitrogen, oxygen, carbon dioxide and halogenated anesthesia gases.

14. A method according to claim 13 wherein said gases are sampled by means connected to the airway of a patient.

15. A method according to claim 11 wherein the gas sample is contained in a gas cell having opposing parallel end windows interconnected by a continuous sidewall, said end windows and sidewall defining a longitudinal gas chamber oriented such that, when gas sample is subjected to said laser beam, the laser beam is coincident with and traverses the axis of said longitudinal gas chamber, said end windows being positioned to be substantially normal to the axis of the longitudinal gas cell chamber, said cell also having opposing, aligned side windows in said sidewall parallel to and on either side of the axis of said longitudinal gas chamber, said gas cell further containing inlet and outlet means communicating with said chamber to pass a sample gas through said cell.

16. A method according to claim 15 wherein said inelastic Raman scattered light and elastic laser scattered light are captured and redirected by said reflection mirror wherein said reflection mirror has a radius of curvature and is located relative to the laser beam at a distance from said beam equal to the radius of curvature of said mirror.

17. A method according to claim 16 wherein said mirror is a spherical mirror.

18. A method according to claim 16 wherein said mirror is a cylindrical mirror.

19. A method according to claim 16 wherein the said end windows in said gas sampling cell are coated with an antireflection coating specific to the wavelength of the laser beam.

20. A method according to claim 16 wherein sample gas is continuously passed through said inlet and outlet means in said gas cell by pump means located in a gas supply line on the inlet side of said gas cell.

* * * * *